(12) United States Patent
Rolbiecki et al.

(10) Patent No.: US 11,331,194 B2
(45) Date of Patent: May 17, 2022

(54) FEMORAL COMPONENT

(71) Applicant: implantcast GmbH, Buxtehude (DE)

(72) Inventors: Patryk Rolbiecki, Apensen (DE); Jens Saß, Buxtehude (DE)

(73) Assignee: implantcast GmbH, Buxtehude (DE)

( * ) Notice: Subject to any disclaimer, the term of this patent is extended or adjusted under 35 U.S.C. 154(b) by 61 days.

(21) Appl. No.: 17/031,115

(22) Filed: Sep. 24, 2020

(65) Prior Publication Data

US 2021/0177610 A1 Jun. 17, 2021

(30) Foreign Application Priority Data

Dec. 17, 2019 (EP) .................................... 19217195

(51) Int. Cl.
*A61F 2/38* (2006.01)
*A61F 2/30* (2006.01)

(52) U.S. Cl.
CPC .......... *A61F 2/3854* (2013.01); *A61F 2/3859* (2013.01); *A61F 2002/3863* (2013.01);
(Continued)

(58) Field of Classification Search
None
See application file for complete search history.

(56) References Cited

U.S. PATENT DOCUMENTS

| 5,824,105 A * | 10/1998 | Ries .................... A61F 2/3859 623/20.31 |
| 6,056,779 A | 5/2000 | Noyer et al. |

(Continued)

FOREIGN PATENT DOCUMENTS

EP 2588032 A1 5/2013

OTHER PUBLICATIONS

European communication dated Jun. 5, 2020 in corresponding European patent application No. 19217195.7 (Europe).

*Primary Examiner* — Ann Schillinger
(74) *Attorney, Agent, or Firm* — Nields, Lemack & Frame, LLC

(57) ABSTRACT

A femoral component (2) for mounting onto a femur and being adapted to articulate with a tibial bearing component in a knee prosthesis comprises proximal end portions (7, 10) adapted to be oriented towards the femur when the femoral component (2) is mounted thereon, and distal end portions adapted to be oriented towards the tibial bearing component when the knee prosthesis is fully extended. The proximal end portions (7) comprise posterior proximal end portions which are located on an posterior side of the femoral component and an anterior proximal end portion (10) which is located on an anterior side of the femoral component (2). The femoral component (2) further comprises a medial condyle (13) and a lateral condyle (14) which each extend from one of the posterior proximal end portions beyond the distal portions and towards the anterior proximal end portion (10) of the femoral component (2). The medial and lateral condyles (13, 14) form a condylar gap between each other, wherein the medial condyle (13) and the lateral condyle (14) are shaped to articulate with the tibial bearing component through a range of motion, in which a full extension of the knee prosthesis corresponds to zero degrees flexion of the knee prosthesis and positive flexion corresponds to greater than zero degrees flexion of the knee prosthesis. The femoral component (2) further comprises a sagittal plane extending in a proximal/distal direction and further extending through the condylar gap from the anterior side to the posterior side of the femoral component (2). A patellar groove (16) extends from the condylar gap towards the anterior proximal end portion (10) of the femoral component (2) along a math- (Continued)

Figure 1:
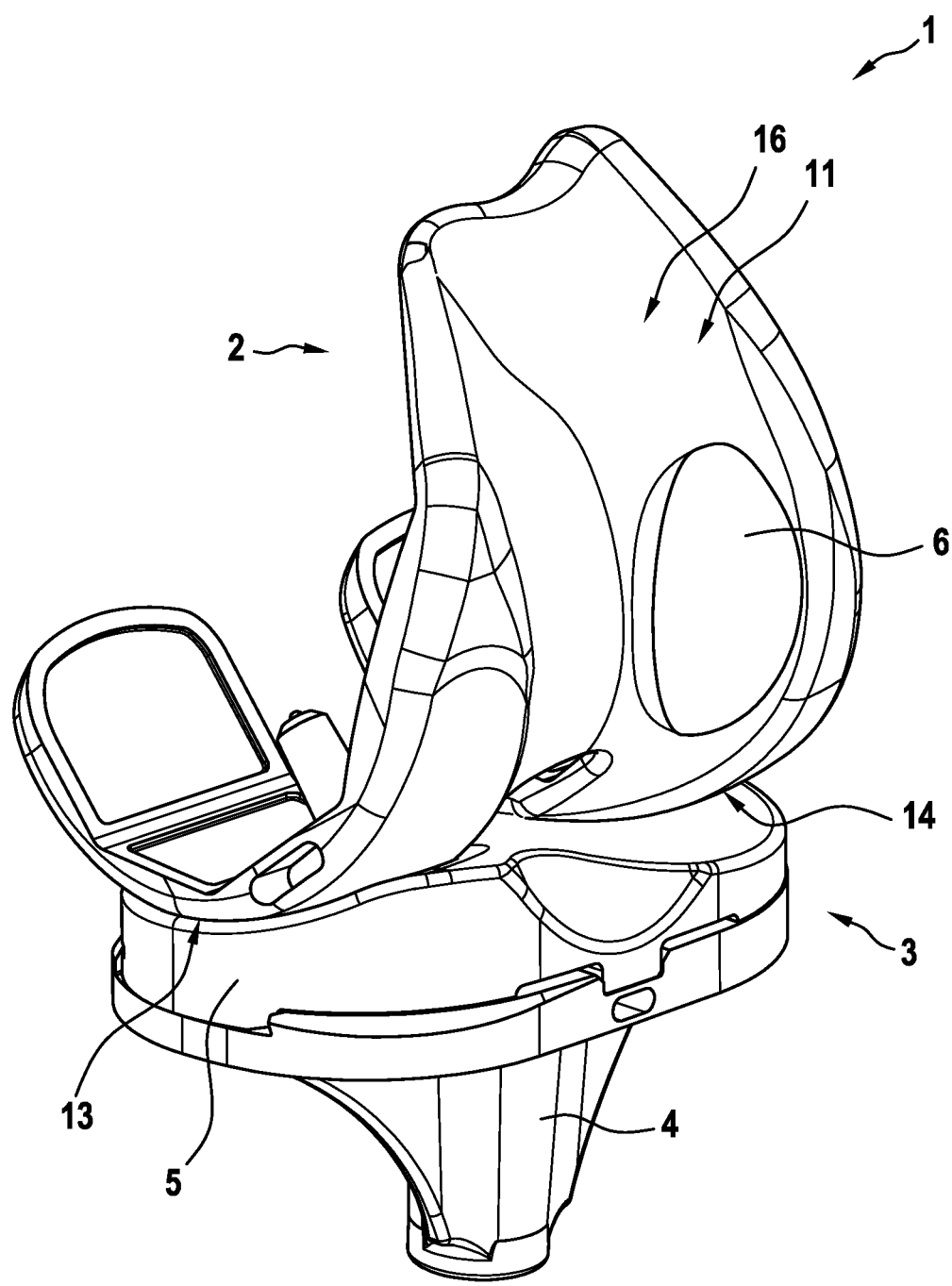

ematical curve (17). The mathematical curve (17), when looking onto the anterior side of the femoral component, is canted towards a medial side (18) of the femoral component (2) relative to the sagittal plane when the patellar groove (16) extends proximally.

The patellar groove (16) is formed by a concave groove section (19) on the anterior side of the femoral component (2), the groove section (19) having a groove base (20). The femoral component (2) further comprises a medial ridge section (21) and a lateral ridge section (22) which are disposed adjacent the groove section (19) and each have a convex shape. The medial ridge section (21) forms the medial condyle (13) and a medial extension (23) to the medial condyle (13) towards the anterior proximal end portion (10). The lateral ridge section (22) forms the lateral condyle (14) and a lateral extension (24) to the lateral condyle (13) towards the anterior proximal end portion (10) of the femoral component (2). The patellar groove (16) has opposing groove edges (25) located at a transition of the concave groove section (19) and the adjacent convex medial ridge section (21) as well as at a transition of the concave groove section (19) and the adjacent lateral ridge section (22). A width (W) of the patellar groove (16) is defined by a distance between the opposing groove edges (25) transverse to the mathematical curve (17). A depth of the patellar groove (16) is defined between the groove base (20) and the medial ridge section (21) or the lateral ridge section (22) normal to the anterior side of the femoral component (2) and parallel to the sagittal plane.

A normal distance from the sagittal plane to the mathematical curve (17), as a function of the length of path of the mathematical curve (17) relative to its starting point at the condylar gap, changes in a non-linear way along the mathematical curve (17) from the condylar gap up to the anterior proximal end portion (10) of the femoral component (2). The width (W) of the patellar groove (16) increases along the patellar groove (16) extending from the condylar gap up to the proximal end portion (10) of the femoral component (2). The depth of the patellar groove (16) decreases along the patellar groove (16) extending from the condylar gap up to the proximal end portion (10) of the femoral component (2).

18 Claims, 4 Drawing Sheets

(52) U.S. Cl.
CPC ............... *A61F 2310/00017* (2013.01); *A61F 2310/00029* (2013.01)

(56) References Cited

U.S. PATENT DOCUMENTS

| | | | |
|---|---|---|---|
| 6,102,955 | A | 8/2000 | Mendes et al. |
| 2014/0142713 | A1* | 5/2014 | Wright ................. A61F 2/3859 623/20.21 |
| 2015/0088264 | A1 | 3/2015 | Li et al. |
| 2015/0257889 | A1* | 9/2015 | Kang ................... A61F 2/3886 623/20.28 |
| 2018/0055647 | A1* | 3/2018 | Murray ................. A61F 2/389 |

\* cited by examiner

FEMORAL COMPONENT

TECHNICAL FIELD

The present invention relates to the field of knee prostheses. In particular the present invention relates to a femoral component for mounting onto a femur and being adapted to articulate with a tibial bearing component in a knee prosthesis, preferably in a medial pivot knee prosthesis.

BACKGROUND OF THE INVENTION

Orthopedic prostheses are commonly utilized to repair and/or replace damaged bone and tissue in the human body. In a total knee arthroplasty procedure, anterior, distal, and posterior portions of the natural femur are resected. A femoral component including medial and lateral condyles, joined together by an anterior patellar flange, is then installed in place of the resected bone. A femoral sulcus (also referred to as a patellar or trochlear groove) is located on the patella flange. The tibia is also resected and a tibial bearing component is installed on the resected bone. The femoral component as well as the tibial bearing component are designed such that the femoral component articulates with the tibial bearing component during flexion and extension of the knee. Moreover, the patellar groove articulates with a patella during flexion and extension of the knee.

Knee prosthesis can be classified according to their kinematics in different ways such as cruciate retaining (CR), medial pivot (MP), lateral pivot (LP) knee prosthesis, posterior stabilized (PS) and other. In general the collateral ligaments and the joint capsule of the natural knee have to be intact for use in primary knee replacement. The anterior cruciate ligament has to be removed, whereas removal or conservation of the posterior cruciate ligament depends on the design of the prosthesis. In primary knee replacement the main stabilizing ligaments are the collateral medial and lateral ligaments, whereas in revision prosthesis all ligaments are replaced by a constrained mechanism provided by the implant.

Medial pivot knee prostheses are based on the natural knee kinematic. The natural knee flexion performs a rotational movement around the medial condyle up to a medium degree of knee flexion. Only in lower degrees of knee flexion there is a uniform role-slide movement between the femur and the tibia. This natural kinematic is realized by the design of the medial pivot prosthesis in which the medial condyle of the femoral component and the tibial bearing component form a ball and socket connection. Due to this connection the medial condyle rotates about a vertical axis located in the centre of the ball and socket connection during flexion of the knee prosthesis. The lateral condyle is configured such that upon flexion of the knee prosthesis the lateral condyle slides onto the tibial bearing component in a posterior direction.

EP 2 588 032 B1 discloses a femoral component for use in an orthopaedic knee prosthesis, the femoral component having a patellar groove which defines a medial planted patella axis when viewed from an anterior side of the femoral component. This document in particular relates to a posterior stabilizing femoral component design and a cruciate femoral component design. Cruciate retaining knee prosthesis are characterized by symmetric medial and lateral condyles. Accordingly, the corresponding inlay on the tibial bearing component is also symmetric to a sagittal plane. Upon rotation of a femoral component of a cruciate retaining knee prosthesis the rotation midpoint is positioned in the center of the tibia. Translatory movement of the femoral component relative to the tibial bearing component takes place uniformly at the condyles. Due to a rather deep shape of the patellar groove of cruciate retaining femoral components the patella is often forced into an unnatural path causing pain in an anterior knee region (patella pain).

It is an object of the present invention to provide a femoral component, in particular for use in a medial pivot knee prosthesis, which avoids pain in an anterior knee region (patella pain) after a total knee athroplasty.

SUMMARY OF THE INVENTION

This object is achieved by a femoral component comprising the features of claim 1. Preferred embodiments are set out in the dependent claims.

According to the present invention a normal distance from the sagittal plane to the mathematical curve, as a function of the length of path of the mathematical curve relative to its starting point at the condylar gap, changes in a non-linear way along the mathematical curve from the condylar gap up to the proximal end portion of the femoral component. In other words, when following the mathematical curve from its starting point at the condylar gap to the anterior proximal end portion of the femoral component, the normal distance to the sagittal plane changes in a non linear way. Yet in other words, the mathematical curve is non-linear when being projected in a coronal plane which is tangent to the most posterior points of the medial and lateral condyles and which extends in a proximal/distal direction. Preferably, the mathematical curve defines the extension of a groove base of the patellar groove. Moreover, as the patellar groove is configured to guide the patella, the mathematical curve preferably also defines the location of the patella.

In connection with the present invention the term "normal" is understood as a three-dimensional relationship in which an auxiliary line, e.g. in order to measure a distance, forms a 90 degree angle to the corresponding plane. e.g. the sagittal plane, from all perspectives. Moreover, in connection with the present invention the term "mathematical curve" is understood as the graph of a mathematical function, wherein the mathematical curve, when projected onto a plane, may show one or multiple inflection points. Consequently, in connection with the present invention the term "mathematical curve" includes for example lines as well as parables of second and higher order.

Furthermore, according to the present invention, the width of the patellar groove increases along the patellar groove extending from the condylar gap up to a proximal end portion of the femoral component and the depth of the patellar groove decreases along the patellar groove extending from the condylar gap up to the proximal end portion of the femoral component. Consequently, during movement of the knee prosthesis from a certain degree of flexion towards full extension of the knee prosthesis, guidance of the patella by the patellar groove decreases and thus the forces acting from the patellar groove on the patella decrease as well.

In connection with the present invention the formulation "the width/depth increases/decreases along the patellar groove" is understood as a continuous increase of the width and a continuous decrease of the depth starting at a certain area or a certain point along the mathematical curve from the condylar gap to the anterior proximal end portion of the femoral component. The position of the certain area or point may also be defined by the position of the patella at a certain degree of flexion of the knee prosthesis. Preferably, the continuous increase/decrease of the width/depth of the patellar groove starts at an area at which the patella is located between 50 to 70 degrees of flexion, more preferably at 60 degrees of flexion of the knee prosthesis.

The combination of the non-linear shape of the mathematical curve/groove base, the increase of the depth of the patellar groove towards the full extension of the knee prosthesis as well as the increasing width of the patellar groove towards the full extension of the knee prosthesis supports the natural movement of the patella during flexion of a knee prosthesis.

The present invention is not limited to medial pivot knee prostheses but can also be used in connection with other knee prostheses such as cruciate retaining (CR) or posterior stabilizes (PS) knee prostheses in order to support the natural movement of the patella during flexion of the knee prosthesis.

In an embodiment according to the present invention the mathematical curve starts in a normal lateral distance to the sagittal plane, intersects the sagittal plane and deviates from the sagittal plane towards the medial side of the femoral component when the patellar groove extends from the condylar gap towards the anterior proximal end of the femoral component. Preferably, the normal lateral distance at the starting point of the mathematical curve at the condylar gap is 4 mm. As every patient which may receive a knee prosthesis differs in size and anatomy, the extension of the patellar groove cannot be reduced to a standard. In general femoral and tibial bearing components are offered by the manufactures in sets or series, wherein each set or series comprises multiple femoral and tibial bearing component combinations which differ in their sizes. Thus, given dimensions of a femoral component or a tibial bearing component relate to one femoral and tibial bearing component combination out of a series.

For example the mathematical curve of a size 6 of a femoral component according to the present invention preferably has the following dimensions when describing the extension of the mathematical curve in terms of the patella position as a function of the degree of flexion of the knee prosthesis. At 90 degrees flexion of the knee prosthesis the patella has a normal lateral distance to the sagittal plane of 7.5 mm. Moreover, the patella lies in the sagittal plane between 20 to 25 degrees of flexion, more preferably in between 22 and 24 degrees of flexion of the knee prosthesis. Optionally, the normal lateral distance of the patella to the sagittal plane in a full extension of the knee prosthesis is 5 mm in medial direction.

In another embodiment according to the present invention the patellar groove is designed to guide the patella during the flexion of the knee prosthesis, and the patellar groove is further designed such that the width of the patellar groove increases while the depth of the patellar groove decreases in an area in which the patella is guided by the patellar groove in between 60 and −20 degrees flexion, in particular in between 60 and −10 degrees flexion of the knee prosthesis. Patients having undergone a total knee arthroplasty using conventional knee prosthesis often report pain in an anterior knee region (patella pain). Causes of this patella pain may be traced back to a strong guidance of the patella by the patellar groove. According to the present invention a reduction of the depth of the patellar groove as well as an increase of the width of the patellar groove leads to a reduction in the guidance of the patella by the patellar groove. Accordingly, in full extension of the knee prosthesis there is only little up to no guidance of the patella by the patellar groove. Consequently, fewer forces compared to conventional designs act on the patella in between preferably −10 to 50 degrees flexion of the knee prosthesis which thus reduces patella pain. Preferably, the patella groove additionally extends from the start of the condylar gap towards the posterior proximal end portions of the femoral component in an area in which the patella is guided by the patella groove up to 105 degrees flexion, preferably up to 100 degrees flexion of the knee prosthesis. From the start of the condylar gap, which corresponds to a position of the patella at around 85 degrees of flexion of the knee prosthesis, up to a position of the patella at around 100 degree flexion of the knee prosthesis the patella groove does not comprise a groove base. In this range of motion guidance of the patella is provided by a concave groove section of the patella groove which is formed by opposing concave inner sidewalls of the medial and lateral condyles.

Preferably, the patellar groove is further designed such that the width of the patellar groove linearly increases while the depth of the patellar groove linearly decreases in an area in which the patella is guided by the patellar groove in between 60 and −20 degree flexion, in particular in between 60 and −10 degrees flexion of the knee prosthesis. Linear increase/decrease allows a constant change of the depth as well as the width of the patellar groove towards full extension of the knee prosthesis.

In an embodiment of the present invention the patellar groove is designed such that its width and its depth in an area in which the patella is located in between −10 and 10 degrees flexion of the knee prosthesis take such values such that there is lower guidance of the patella by the patellar groove compared to an area in which the patella is located in between 10 and 85 degrees flexion of the knee prosthesis. In other words, in between −10 and 10 degrees flexion of the knee prosthesis the patella remains unguided by the patellar groove. The patella may freely move on the femoral component in proximity to the anterior proximal end portion. No or nearly no forces act from the patellar groove onto the patella.

In another embodiment of the present invention the patellar groove is further designed such that its depth remains constant in an area in which the patella is guided by the patellar groove in between 60 and 100 degrees flexion, in particular in between 60 and 85 degrees flexion of the knee prosthesis. In the area of a constant depth of the patellar groove the patella is guided by the patellar groove and thus luxation of the patella from the patellar groove is avoided. In the area of a constant depth of the patellar groove forces act from the patellar groove onto the patella in order to provide a proper movement of the patella according to the patellar groove. Preferably, the area of flexion between −20 to 100 degrees flexion of the knee prosthesis is subdivided in the area of constant depth of the patellar groove (60 degrees to 100 degrees) and the area of increasing width as well as of decreasing depth of the patellar groove (−20 degrees to 60 degrees). Consequently, both areas are positioned adjacent to one another. In other words, both areas adjoin to each other.

In an embodiment of the present invention the mathematical curve when being projected onto the sagittal plane forms a sector of a first circle in an area in which the patella is guided by the patellar groove in between 60 and 100 degrees flexion, in particular in between 60 and 85 degrees flexion of the knee prosthesis. In other words, the mathematical curve when being projected onto the sagittal plane has a constant first radius in an area in which the patella is guided by the patellar groove in between 60 and 100 degrees flexion, in particular in between 60 degrees flexion of the knee prosthesis up to the start of the condylar gap, which corresponds to 85 degrees flexion of the knee prosthesis. This concept may be also realized in combination with other femoral components independently of the present invention as claimed in claim 1.

In another embodiment of the present invention the concave groove section when being intersected by a sectional plane which extends normal to the anterior side of the femoral component and in a medial/lateral direction forms a sector of a second circle in an area in which the patella is guided by the patellar groove in between 60 and 100 degrees flexion, in particular in between 60 and 85 degrees flexion of the knee prosthesis. When following the mathematical curve from its starting point at the condylar gap to the anterior proximal end portion of the femoral component in an area in which the patella is guided by the patellar groove in between 60 and 85 degrees flexion of the knee prosthesis the concave groove section has a constant second radius in a sectional plane extending normal to the anterior side of the femoral component and extending in a medial/later direction. In other words, in an area in which the patella is guided by the patellar groove in between 60 and 85 degrees flexion of the knee prosthesis, the radiuses of the concave groove section at different locations along the mathematical curve, at which the concave groove section is intersected by a sectional plane extending normal to the anterior side of the femoral component and in a medial/lateral direction, correspond to each other.

Preferably, the patella groove and thus also the concave groove section additionally extend in an area in which the patella is guided by the patella groove in between 85 degrees of flexion of the knee prosthesis, which corresponds to the start of the condylar gap, and 100 degrees flexion of the knee prosthesis. Accordingly, the concave groove section when being intersected by a sectional plane which extends normal to the anterior side of the femoral component and in a medial/lateral direction also forms a sector of the second circle in an area in which the patella is guided by the patellar groove in between 85 and 100 degrees flexion of the knee prosthesis. However, in the area in which the patella is guided by the patellar groove in between 85 and 100 degrees flexion of the knee prosthesis, the concave groove section of the patella groove does not comprise a groove base. In this area the concave groove section is formed by opposing concave inner sidewalls of the medial and lateral condyles. The above described concepts may be also realized in combination with other femoral components independently of the present invention as claimed in claim 1.

Preferably the sector of the first circle comprises a first radius and the sector of the second circle comprises a second radius, wherein the first radius and the second radius correspond to each other. The advantage of the constant, corresponding first and second radiuses is that a constant guidance of the patella is provided in between 60 and 100 degrees flexion, preferably in between 60 and 85 degrees flexion of the knee prosthesis, which allows a natural movement of the patella and thus minimizes patella pain. This concept may be also realized in combination with other femoral components independently of the present invention as claimed in claim 1. Preferably, the medial condyle is shaped to engage with the tibial bearing component in a ball and socket connection, wherein the lateral condyle is shaped to freely move in a posterior direction relative to the tibial bearing component upon flexion of the knee prosthesis. In other words the femoral component is adapted to be used in combination with a tibial bearing component in medial pivot knee prosthesis. Medial pivot knee prostheses are configured to provide natural movement of the patella during flexion of the knee prosthesis.

In an embodiment of the present invention the medial condyle is shaped to engage with the tibial bearing component in a ball and socket connection in between −10 and 110 degrees flexion of the knee prosthesis and that the medial condyle is shaped such that the ball and socket connection is released above 110 degrees flexion of the knee prosthesis. Medial pivot knee prostheses are characterized by a first area of flexion on which the femoral component is connected with the tibial bearing component via a ball and socket connection, whereas in a second are of flexion this connection is released to provide a translatory movement of the femur relative to the tibia.

In another embodiment of the present invention the femoral component is formed of a cobalt chrome alloy and/or stainless steel. Cobalt chrome alloys and/or stainless steel have been shown to be body compatible.

The above object is also achieved by a knee prosthesis comprising the features of claim 10. According to the present invention the knee prosthesis comprises a femoral component as described above and a tibial bearing component.

In an embodiment of the present invention the tibial bearing component comprises a tibial component for mounting onto a tibia and an inlay which is located between the femoral component and the tibial component and with which the medial condyle and the lateral condyle of the femoral component articulate. Preferably, the femoral component is made from a cobalt chrome alloy and/or stainless steel, whereas the inlay is formed from polyethylene (PE).

In another embodiment of the present invention the knee prosthesis is a medial pivot knee prosthesis. Medial pivot knee prostheses realize a natural knee kinematic, in particular a natural movement of the patella in the patellar groove.

Figure 2:
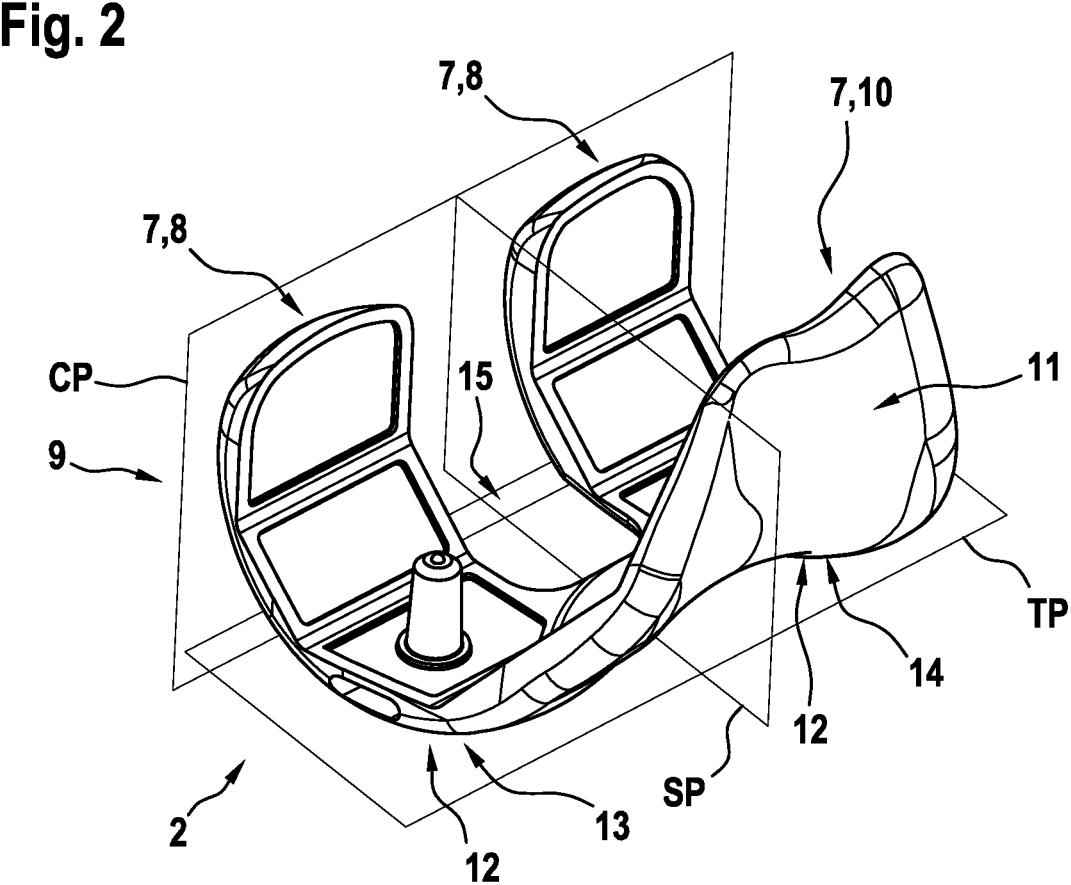
Figure 3:
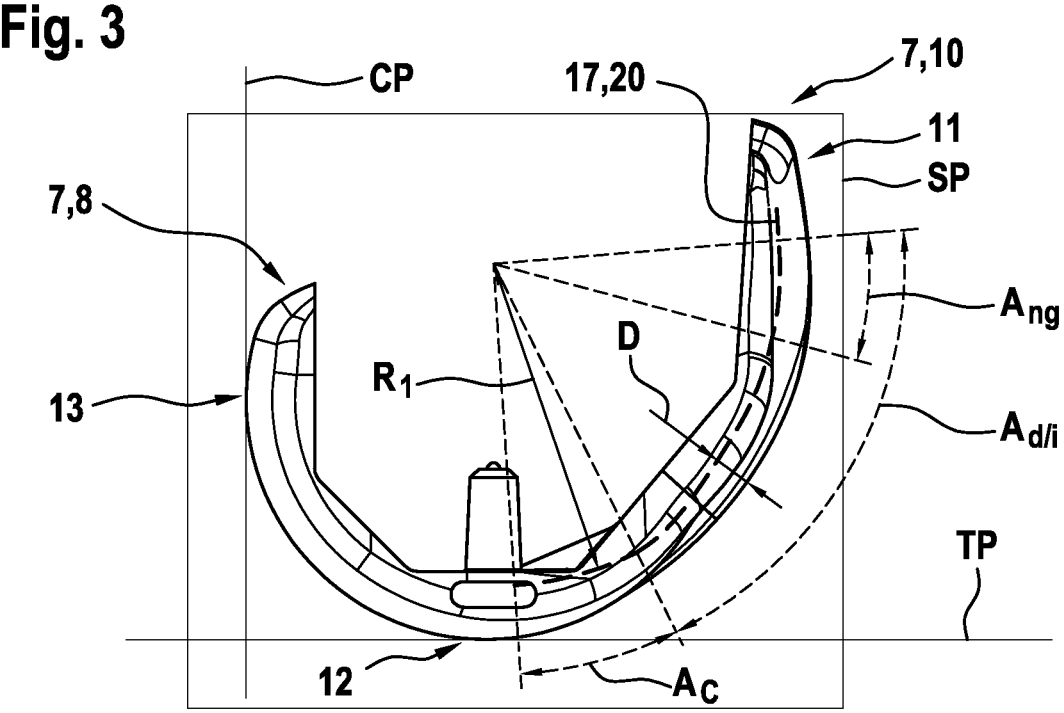
Figure 4:
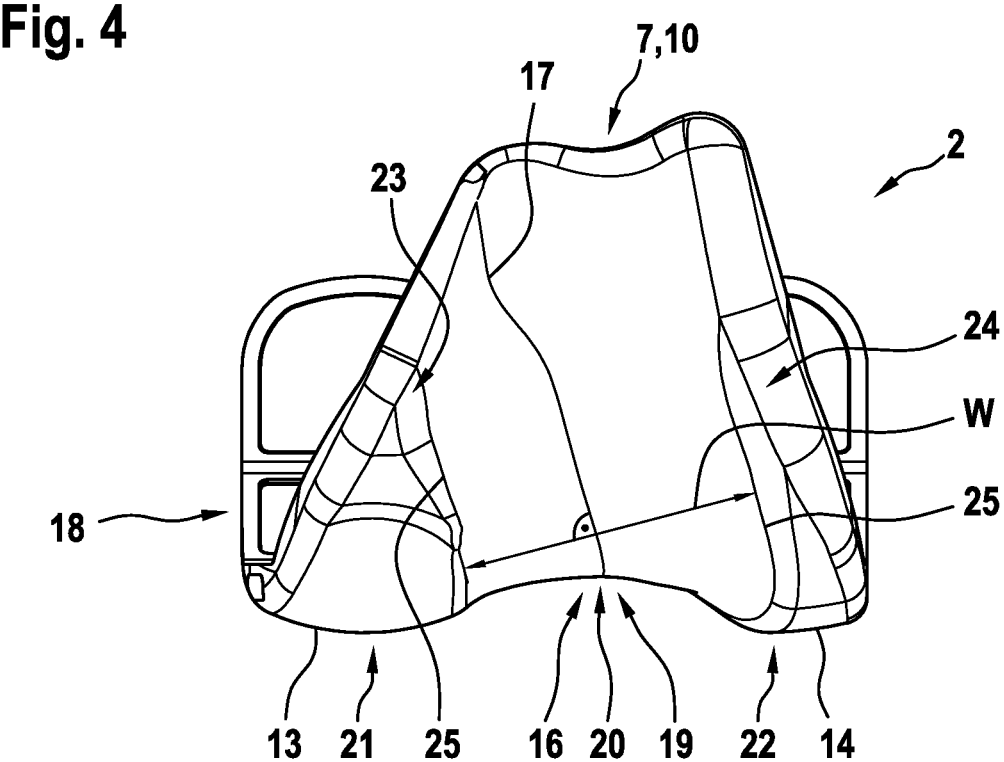
Figure 5:
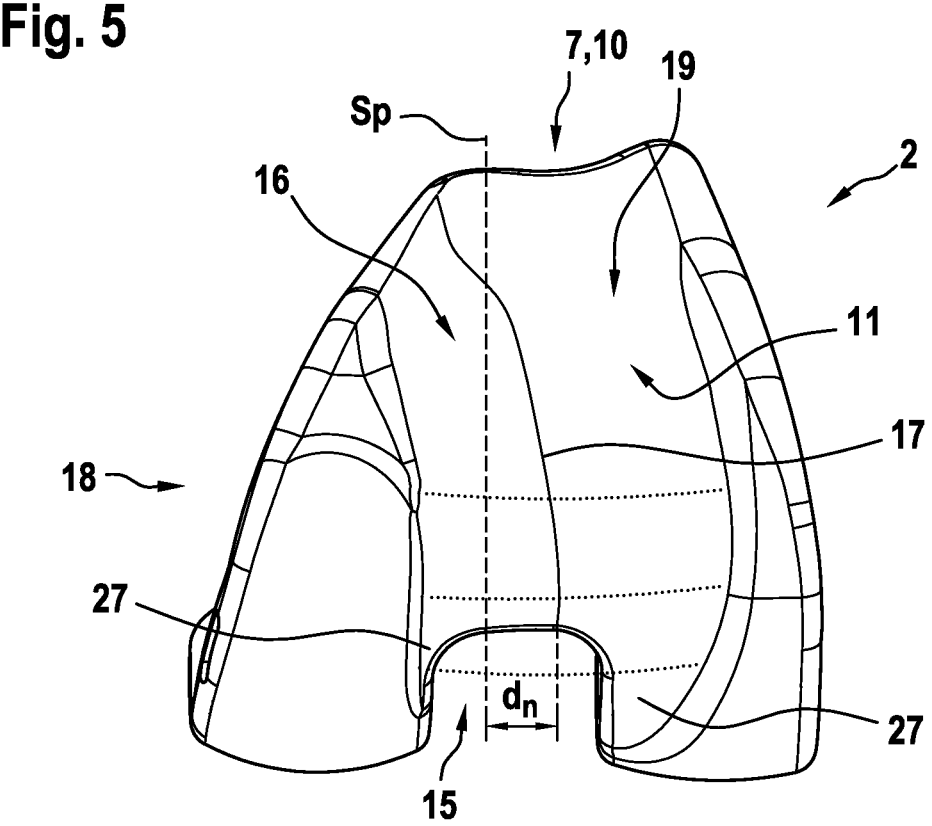
Figure 6:
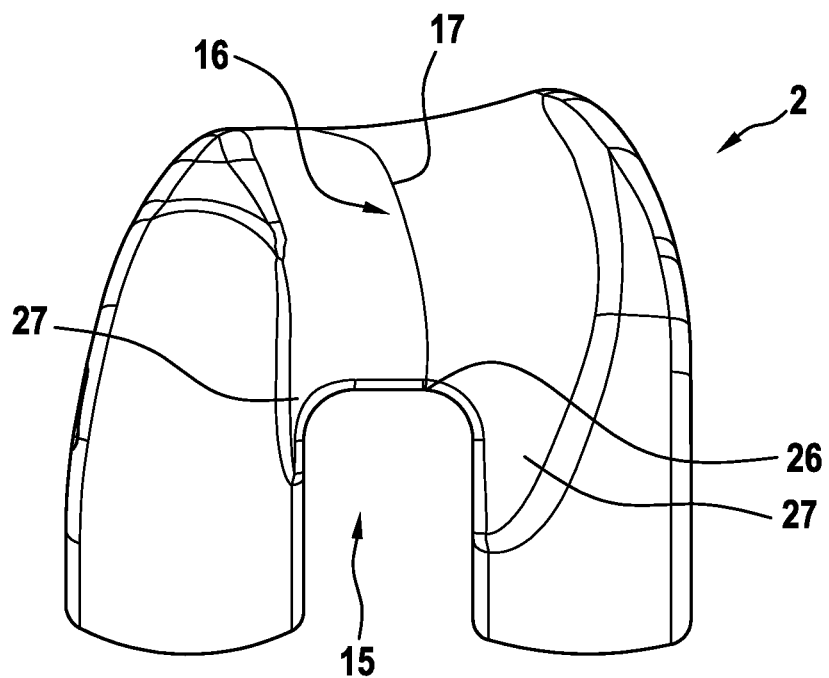

The invention will now be described in connection with one exemplary embodiment shown in the figures in which:

FIG. 1 shows a medial pivot knee prosthesis together with a patella in an isometric view, FIG. 2 shows an isometric view of a femoral component in full extension, FIG. 3 shows a femoral component in full extension in a side view with the groove base shown as a dotted line, FIG. 4 shows a front view of a femoral component in full extension, FIG. 5 shows a femoral component in 30 degrees flexion in a front view and FIG. 6 shows a femoral component in 90 degrees flexion in a front view.

FIG. 1 shows a knee prosthesis 1 formed as a medial pivot knee prosthesis. The knee prosthesis 1 comprises a femoral component 2 for mounting onto a femur (not shown) and being adapted to articulate with a tibial bearing component 3 in the knee prosthesis 1. The tibial bearing component 3 is formed by a tibial component 4 for mounting onto a tibia (not shown) and an inlay 5. The inlay 5 is located between the femoral component 2 and the tibial component 4 and is connected to the tibial component 4. The inlay 5 is made from polyethylene (PE).

The femoral component 2 is formed of a cobalt chrome alloy and/or stainless steel and comprises a medial condyle 13 and a lateral condyle 14. The medial condyle 13 and the lateral condyle 14 are shaped to articulate with the tibial bearing component 3 through a range of motion, in which a full extension of the knee prosthesis 1 corresponds to 0 degrees flexion of the knee prosthesis 1 and positive flexion corresponds to greater than 0 degrees flexion of the knee prosthesis 1. Accordingly, negative flexion corresponds to below 0 degrees flexion of the knee prosthesis 1.

The medial condyle 13 is further shaped to engage with the tibial bearing component 3 in a ball and socket connection, wherein the lateral condyle 14 is shaped to freely move in a posterior direction relative to the tibial bearing component upon flexion of the knee prosthesis 1. In particular, the medial condyle 13 is shaped to engage with the tibial bearing component 3 in a ball and socket connection in between −10 and 110 degrees flexion of the knee prosthesis. The medial condyle 13 is further shaped such that the ball and socket connection is released above 110 degrees flexion of the knee prosthesis 1.

A patella 6 is located anterior to the femoral component 2 and abuts the same. The patella 6 may be a natural or a prosthetic patella. The patella 6 is held in place by the quadriceps (not shown) which is fixed to the tibia and the femur (not shown) and is guided by a patellar groove 16 located on an anterior side 11 of the femoral component 2.

FIGS. 2 and 3 show the femoral component 2 in detail. The femoral component 2 comprises proximal end portions 7 adapted to be oriented towards the femur when the femoral component 2 is mounted thereon. The proximal end portions 7 comprise posterior proximal end portions 8 which are located on a posterior side 9 of the femoral component 2. The proximal end portions 7 also comprise an anterior proximal end portion 10, which is located on the anterior side 11 of the femoral component 2.

The femoral component 2 further comprises distal end portions 12 adapted to be oriented towards the tibial bearing component (FIG. 1) when the knee prosthesis is fully extended.

The medial condyle 13 and the lateral condyle 14 of the femoral component 2 each extend from one of the posterior proximal end portions 8 beyond the distal portions 12 and towards the anterior proximal end portion 10 of the femoral component 2. The medial condyle 13 and the lateral condyle 14 form a condylar gap 15 between each other.

The femoral component 2 further comprises a coordinate system in which a sagittal plane SP extends in proximal/distal direction and further extends through the condylar gap 15 from the anterior side 11 to the posterior side 9 of the femoral component 2. A coronal plane CP is tangent to the posterior most points of the medial and lateral condyles 13, 14 and extends in the proximal/distal direction. The coronal plane CP is located perpendicular to the sagittal plane SP. A transverse plane TP is tangent to the distal end portions 12 of the femoral component 2 and extends from the anterior side 11 to the posterior side 9 of the femoral component 2. The transverse plane TP is perpendicular to the sagittal plane SP and to the coronal plane CP.

FIGS. 4 to 6 show the femoral component 2 in more detail. For a better understanding of the geometry of the femoral component 2 FIGS. 4 to 6 additionally show surface lines on the anterior side 11 of the femoral component 2.

The patellar groove 16 of the femoral component 2 extends from the condylar gap 15 towards the anterior proximal end portion 10 of the femoral component 2 along a mathematical curve 17. The mathematical curve 17, when looking onto the anterior side 11 of the femoral component 2, as for example shown in FIGS. 4 to 6, is canted towards a medial side 18 of the femoral component 2 relative to the sagittal plane SP (shown as a dotted line in FIG. 5) when the patellar groove 16 extends proximally.

The patellar groove 16 is formed by a concave groove section 19 on the anterior side 11 of the femoral component 2. The groove section 19 has a groove base 20. The extension of the groove base 20 defines the mathematical curve 17 from the condylar gap 15 towards the anterior proximal end portion 10.

The patella groove 16 additionally extends from a start of the condylar gap 15, which corresponds to a position of the patella 6 at around 85 degrees of flexion of the knee prosthesis 1, towards the posterior proximal end portions 8 of the femoral component 2 in an area in which the patella 6 is guided by the patella groove 16 between 85 and 100 degrees flexion of the knee prosthesis 1. From the start of the condylar gap 15 up to a position of the patella 6 at around 100 degree flexion of the knee prosthesis 1 the patella groove 16 does not comprise a groove base 20. In this range of motion guidance of the patella 6 is provided by the concave groove section 19 of the patella groove 16 which is formed by opposing concave inner sidewalls 27 of the medial and lateral condyles.

The femoral component 2 further comprises a medial ridge section 21 and a lateral ridge section 22 which are disposed adjacent to the groove section 19 and each have a convex shape. The medial ridge section 21 forms the medial condyle 13 and a medial extension 23 to the medial condyle 13 towards the anterior proximal end portion 10. The lateral ridge section 22 forms the lateral condyle 14 and a lateral extension 24 to the lateral condyle 14 towards the anterior proximal end portion 10 of the femoral component 2.

The patellar groove 16 has opposing groove edges 25 located at a transition of the concave groove section 19 and the adjacent convex medial ridge section 21 as well as at a transition of the concave groove section 19 and the adjacent lateral ridge section 22.

A width W of the patellar groove 16 is defined by a distance between the opposing groove edges 25 transverse to the vertical curve 17. Moreover, a depth D (see FIG. 3) of the patellar groove is defined between the groove base 20 and the medial ridge section 21 or the lateral ridge section 22 normal to the anterior side 11 of the femoral component 2 and parallel to the sagittal plane SP.

As can be seen in particular in FIG. 5 a normal distance $d_n$ from the sagittal plane SP to the mathematical curve 17, as a function of the length of path of the mathematical curve relative to its starting point 26 at the condylar gap 15 (see FIG. 6), changes in a non-linear way along the mathematical curve 17 from the condylar gap 15 up to the anterior proximal end portion 10 of the femoral component 2. The mathematical curve 17 starts in a normal lateral distance to the sagittal plane SP at its starting point 26, intersects the sagittal plane SP and deviates from the sagittal plane SP towards the medial side 18 of the femoral component 2 when the patellar groove 16 extends from the condylar gap 15 towards the anterior proximal end portion 10 of the femoral component 2.

The femoral component 2 as shown in FIG. 5 constitutes a femoral component 2 of a series of femoral components which differ in their sizes. In particular, the femoral component 2 as shown in FIG. 5 has a distance $d_n$ of 4 mm at which the mathematical curve 17 is located lateral and normal to the sagittal plane SP.

As can be seen in particular in FIG. 3 the patellar groove 16 is designed such that its depth D remains constant in an area $A_c$ in which the patella 6 (FIG. 1) is guided by the patellar groove 16 in between 60 and 85 degrees flexion of the knee prosthesis 1.

The patellar groove is further designed such that the width W of the patellar groove 16 linearly increases and the depth D of the patellar groove 16 linearly decreases in an area $A_{d/i}$ in which the patella 6 is guided by the patellar groove 16 in between 60 and −10 degrees flexion of the knee prosthesis 1.

The area of flexion between −10 to 85 degrees flexion of the knee prosthesis 1 is subdivided in the area $A_c$ of constant depth D of the patellar groove 16 (60 degrees to 85 degrees) and the area $A_{d/i}$ of increasing width W as well as of decreasing depth D of the patellar groove 16 (−10 degrees to 60 degrees). Both areas $A_c$, $A_{d/i}$ adjoin to each other.

Moreover, the patellar groove 16 is designed such that its width W and its depth D in an area $A_{ng}$ in which the patella 6 is located in between −10 and 10 degrees flexion of the knee prosthesis 1 take such values such that there is no guidance of the patella 6 by the patellar groove 16.

As can be seen in particular in FIG. 3, the mathematical curve 17 when being projected onto the sagittal plane SP forms a sector of a first circle having a constant first radius $R_1$ in the area $A_c$ (60 degrees to 85 degrees) of the patella groove 16.

Moreover, as can be seen in particular in FIG. 5 the concave groove section 19, when being intersected at different locations along the mathematical curve 17 by multiple different sectional planes (not shown), which each extend normal to the anterior side 11 of the femoral component 2 and in a medial/lateral direction, forms a sector of a second circle (shown in FIG. 5 in dotted lines) at each of the different positions in the area $A_c$ (FIG. 3, 60 degrees to 85 degrees) of the patella groove 16.

As mentioned above the patella groove 16 and thus also the concave groove section 19 additionally extend in an area in which the patella 6 is guided by the patella groove 16 in between 85 degrees and 100 degrees flexion of the knee prosthesis 1 and thus in an area in which the condylar gap 15 is located. Accordingly, the concave groove section 19 when being intersected by a sectional planes (not shown) which extends normal to the anterior side 11 of the femoral component 2 and in a medial/lateral direction also forms a sector of the second circle (shown in FIG. 5 in dotted lines) in an area in which the patella 6 is guided by the patellar groove 16 in between 85 and 100 degrees flexion of the knee prosthesis 1. However, in the area in which the patella 6 is guided by the patellar groove 16 in between 85 and 100 degrees flexion of the knee prosthesis 1, the concave groove section 19 of the patella groove 16 does not comprise a groove base. In this area the concave groove section 19 is formed by opposing concave inner sidewalls 27 of the medial and lateral condyles (13, 14).

The sector of the first circle comprises the first radius $R_1$ and the sector of the second circle comprises a second radius (not sown), wherein the first radius $R_1$ and the second radius correspond to each other.

REFERENCE NUMERALS 1 medial pivot knee prosthesis
2 femoral component
3 tibial bearing component
4 tibial component
5 inlay
6 patella
7 proximal end portion
8 posterior proximal end portion
9 posterior side
10 anterior proximal end portion
11 anterior side
12 distal end portion
13 medial condyle
14 lateral condyle
15 condylar gap
SP sagittal plane
CP coronal plane
TP transverse plane
16 patellar groove
17 mathematical curve
18 medial side
19 concave groove section
20 groove base
21 medial ridge section
22 lateral ridge section
23 medial extension
24 lateral extension
25 groove edges
W width (patellar groove)
D depth (patella grove)
$d_n$ distance
26 starting point
$A_c$ area of constant depth
$A_{d/i}$ area of decreasing depth and increasing width
$A_{ng}$ area of no guidance
27 concave inner sidewalls
$R_1$ first radius

The invention claimed is:

1. Femoral component for mounting onto a femur and being adapted to articulate with a tibial bearing component in a knee prosthesis, wherein the femoral component comprises:
   proximal end portions adapted to be oriented towards the femur when the femoral component is mounted thereon, and distal end portions adapted to be oriented towards the tibial bearing component when the knee prosthesis is fully extended,
   wherein the proximal end portions comprise posterior proximal end portions which are located on a posterior side of the femoral component and an anterior proximal end portion which is located on an anterior side of the femoral component,
   wherein the femoral component further comprises:
   a medial condyle and a lateral condyle which each extend from one of the posterior proximal end portions beyond the distal portions and towards the anterior proximal end portion of the femoral component and which form a condylar gap between each other, wherein the medial condyle and the lateral condyle are shaped to articulate with the tibial bearing component through a range of motion, in which a full extension of the knee prosthesis corresponds to zero degrees flexion of the knee prosthesis and positive flexion corresponds to greater than zero degrees flexion of the knee prosthesis,
   a sagittal plane extending in a proximal/distal direction and further extending through the condylar gap from the anterior side to the posterior side of the femoral component, and
   a patellar groove which extends from the condylar gap towards the anterior proximal end portion of the femoral component along a mathematical curve which, when looking onto the anterior side of the femoral component, is canted towards a medial side of the femoral component relative to the sagittal plane when the patellar groove extends proximally,
   wherein the patellar groove is formed by a concave groove section on the anterior side of the femoral component, the groove section having a groove base,
   wherein the femoral component further comprises a medial ridge section and a lateral ridge section which are disposed adjacent the groove section and each have a convex shape, the medial ridge section forming the medial condyle and a medial extension to the medial condyle towards the anterior proximal end portion, the lateral ridge section forming the lateral condyle and a lateral extension to the lateral condyle towards the anterior proximal end portion of the femoral component, wherein the patellar groove has opposing groove edges located at a transition of the concave groove section and the adjacent convex medial ridge section as well as at a transition of the concave groove section and the adjacent lateral ridge section, wherein a width of the patellar groove is defined by a distance between the opposing groove edges transverse to the mathematical curve, wherein a depth of the patellar groove is defined between the groove base and the medial ridge section or the lateral ridge section normal to the anterior side of the femoral component and parallel to the sagittal plane, wherein a normal distance ($d_n$) from the sagittal plane to the mathematical curve, as a function of the length of path of the mathematical curve relative to its starting point at the condylar gap, changes in a non-linear way along the mathematical curve from the condylar gap up to the anterior proximal end portion of the femoral component, wherein the width of the patellar groove increases along the patellar groove extending from the condylar gap up to the anterior proximal end portion of the femoral component and wherein the depth of the patellar groove decreases along the patellar groove extending from the condylar gap up to the anterior proximal end portion of the femoral component, and wherein the patellar groove is designed to guide a patella during the flexion of the knee prosthesis, and that the patellar groove is further designed such that the width of the patellar groove increases while the depth of the patellar groove decreases in an area in which the patella is guided by the patellar groove in between 60 and −20 degrees flexion of the knee prosthesis, and wherein the patellar groove is further designed such that its depth remains constant in an area in which the patella is guided by the patellar groove in between 60 and 100 degrees flexion of the knee prosthesis.

2. Femoral component according to claim 1, wherein the mathematical curve starts in the normal lateral distance ($d_n$) from the sagittal plane, intersects the sagittal plane and deviates from the sagittal plane towards the medial side of the femoral component when the patellar groove extends from the condylar gap towards the anterior proximal end portion of the femoral component.

3. Femoral component according to claim 1, wherein the patellar groove is further designed such that the width of the patellar groove linearly increases while the depth of the patellar groove linearly decreases in an area in which the patella is guided by the patellar groove in between 60 and −20 degrees flexion of the knee prosthesis.

4. Femoral component according to claim 1, wherein the patellar groove is designed such that its width and its depth in an area in which the patella is located in between −10 and 10 degrees flexion of the knee prosthesis take such values such that there is lower guidance of the patella by the patellar groove compared to an area in which the patella is located in between 10 and 85 degrees flexion of the knee prosthesis.

5. Femoral component according to claim 1, wherein the mathematical curve when being projected onto the sagittal plane forms a sector of a first circle in an area in which the patella is guided by the patellar groove in between 60 and 100 degrees flexion of the knee prosthesis.

6. Femoral component according to claims 5 wherein the sector of the first circle comprises a first radius and the sector of the second circle comprises a second radius, wherein the first radius and the second radius correspond to each other.

7. Femoral component according to claim 1, wherein the concave groove section when being intersected by a sectional plane which extends normal to the anterior side of the femoral component and in a medial/lateral direction forms a sector of a second circle in an area in which the patella is guided by the patellar groove in between 60 and 100 degrees flexion of the knee prosthesis.

8. Femoral component according to claim 1, wherein the medial condyle is shaped to engage with the tibial bearing component in a ball and socket connection, wherein the lateral condyle is shaped to freely move in a posterior direction relative to the tibial bearing component upon flexion of the knee prosthesis.

9. Femoral component according to claim 8, wherein the medial condyle is shaped to engage with the tibial bearing component in a ball and socket connection in between −10 and 110 degrees flexion of the knee prosthesis and that the medial condyle is shaped such that the ball and socket connection is released above 110 degrees flexion of the knee prosthesis.

10. Femoral component according to claim 1, wherein the femoral component is formed of a cobalt chrome alloy and/or stainless steel.

11. Femoral component according to claim 1, wherein the patellar groove is designed to guide a patella during the flexion of the knee prosthesis, and that the patellar groove is further designed such that the width of the patellar groove increases while the depth of the patellar groove decreases in an area in which the patella is guided by the patellar groove in between 60 and −10 degrees flexion of the knee prosthesis.

12. Femoral component according to claim 1, wherein the patellar groove is further designed such that the width of the patellar groove linearly increases while the depth of the patellar groove linearly decreases in an area in which the patella is guided by the patellar groove in between 60 and −10 degrees flexion of the knee prosthesis.

13. Femoral component according to claims 1, wherein the patellar groove is further designed such that its depth remains constant in an area in which the patella is guided by the patellar groove in between 60 and 85 degrees flexion of the knee prosthesis.

14. Femoral component according to claim 1, wherein the mathematical curve when being projected onto the sagittal plane forms a sector of a first circle in an area in which the patella is guided by the patellar groove in between 60 and 85 degrees flexion of the knee prosthesis.

15. Femoral component according to claim 1, wherein the concave groove section when being intersected by a sectional plane which extends normal to the anterior side of the femoral component and in a medial/lateral direction forms a sector of a second circle in an area in which the patella is guided by the patellar groove in between 60 and 85 degrees flexion of the knee prosthesis.

16. Knee prosthesis comprising a femoral component according to claim 1 and a tibial bearing component.

17. Knee prosthesis according to claim 16 wherein the tibial bearing component comprises a tibial component for mounting onto a tibia and an inlay which is located between the femoral component and the tibial component and with which the medial condyle and the lateral condyle of the femoral component articulate.

18. Knee prosthesis according to claim 16, wherein the knee prosthesis is a medial pivot knee prosthesis.

* * * * *